United States Patent
Baldychev et al.

(10) Patent No.: US 10,099,976 B2
(45) Date of Patent: Oct. 16, 2018

(54) INTEGRATED PROCESS FOR THE PRODUCTION OF Z-1,1,1,4,4,4-HEXAFLUORO-2-BUTENE

(71) Applicant: THE CHEMOURS COMPANY FC, LLC, Wilmington, DE (US)

(72) Inventors: Ivan Sergeyevich Baldychev, Wilmington, DE (US); Stephan M Brandstadter, Philadelphia, PA (US); Patricia Cheung, Glen Mills, PA (US); Mario Joseph Nappa, Leesburg, FL (US); Sheng Peng, Hockessin, DE (US); Donald J Toton, New Castle, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 15/699,067

(22) Filed: Sep. 8, 2017

(65) Prior Publication Data
US 2017/0369403 A1    Dec. 28, 2017

Related U.S. Application Data

(62) Division of application No. 15/114,944, filed as application No. PCT/US2015/014783 on Feb. 6, 2015, now Pat. No. 9,758,452.

(60) Provisional application No. 61/937,109, filed on Feb. 7, 2014.

(51) Int. Cl.
| | |
|---|---|
| *C07C 17/25* | (2006.01) |
| *C07C 17/23* | (2006.01) |
| *C07C 17/354* | (2006.01) |
| *C07C 17/281* | (2006.01) |

(52) U.S. Cl.
CPC .............. *C07C 17/25* (2013.01); *C07C 17/23* (2013.01); *C07C 17/281* (2013.01); *C07C 17/354* (2013.01); *Y02P 20/125* (2015.11); *Y02P 20/582* (2015.11)

(58) Field of Classification Search
CPC ......... C07C 17/23; C07C 21/18; C07C 19/01; C07C 19/08; C07C 19/10; C07C 17/25; C07C 17/354; B01J 23/58; B01J 23/72; B01J 23/8926; B01J 23/74
See application file for complete search history.

(56) References Cited

U.S. PATENT DOCUMENTS

| | | |
|---|---|---|
| 5,919,994 A | 7/1999 | Rao |
| 6,348,634 B1 | 2/2002 | Cuzzato et al. |
| 2009/0012335 A1 | 1/2009 | Nappa et al. |
| 2013/0158304 A1* | 6/2013 | Quan ................ B01J 21/04 570/151 |

FOREIGN PATENT DOCUMENTS

| | | |
|---|---|---|
| EP | 25813610 A1 | 4/2013 |
| WO | 199505353 A1 | 2/1995 |

OTHER PUBLICATIONS

International Search Report and Written Opinion, PCT/US2015/014783, dated Jun. 25, 2015.

* cited by examiner

*Primary Examiner* — Jafar F Parsa

(57) ABSTRACT

Disclosed is a process for the preparation of cis-1,1,1,4,4,4-hexafluoro-2-butene comprising contacting 1,1,1-trifluorotrichloroethane with hydrogen in the presence of a catalyst comprising ruthenium to produce a product mixture comprising 1316mxx, recovering said 1316mxx as a mixture of Z- and E-isomers, contacting said 1316mxx with hydrogen, in the presence of a catalyst selected from the group consisting of copper on carbon, nickel on carbon, copper and nickel on carbon and copper and palladium on carbon, to produce a second product mixture, comprising E- or Z-CFC-1326mxz, and subjecting said second product mixture to a separation step to provide E- or Z-1326mxz. The E- or Z-1326mxz can be dehydrochlorinated in an aqueous basic solution with an alkali metal hydroxide in the presence of a phase transfer catalyst to produce hexafluoro-2-butyne, which can then be selectively hydrogenated to produce Z-1,1,1,4,4,4-hexafluoro-2-butene using using either Lindlar's catalyst, or a palladium catalyst further comprising a lantanide element or silver.

12 Claims, No Drawings

INTEGRATED PROCESS FOR THE PRODUCTION OF Z-1,1,1,4,4,4-HEXAFLUORO-2-BUTENE

BACKGROUND INFORMATION

Field of the Disclosure

This disclosure relates in general to methods of synthesis of fluorinated olefins.

Description of the Related Art

The fluorocarbon industry has been working for the past few decades to find replacement refrigerants for the ozone depleting chlorofluorocarbons (CFCs) and hydrochlorofluorocarbons (HCFCs) being phased out as a result of the Montreal Protocol. The solution for many applications has been the commercialization of hydrofluorocarbon (HFC) compounds for use as refrigerants, solvents, fire extinguishing agents, blowing agents and propellants. These new compounds, such as HFC refrigerants, HFC-134a and HFC-125 being the most widely used at this time, have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well as having low global warming potentials. Certain hydrofluoroolefins are believed to meet both goals. Thus there is a need for manufacturing processes that provide halogenated hydrocarbons and fluoroolefins that contain no chlorine that also have a low global warming potential.

SUMMARY

In one embodiment, disclosed is a part of a process for the preparation of cis-1,1,1,4,4,4-hexafluoro-2-butene comprising contacting 1,1,1-trifluorotrichloroethane with hydrogen in the presence of a catalyst comprising ruthenium to produce a product mixture comprising 1316mxx, recovering said 1316mxx as a mixture of Z- and E-isomers, contacting said 1316mxx with hydrogen, in the presence of a catalyst selected from the group consisting of copper on carbon, nickel on carbon, copper and nickel on carbon and copper and palladium on carbon, to produce a second product mixture, comprising E- or Z-CFC-1326mxz, and subjecting said second product mixture to a separation step to provide E- or Z-1326mxz.

In another embodiment, disclosed is a process for the preparation of fluorine-containing olefins comprising contacting a chlorofluoroalkene having the formula E- and Z-$CF_3CCl=CClCF_3$ with hydrogen in the presence of a catalyst comprising copper and palladium on a support, at a temperature of from about 150° C. to 250° C., to produce a product mixture comprising a fluorine-containing olefin having the formula E- or Z-$CF_3CH=CClCF_3$, or a mixture thereof, wherein the conversion of Z-$CF_3CCl=CClCF_3$ is at least 80% of the conversion of the Z-isomer, and the selectivity to the two isomers of $CF_3CH=CClCF_3$ is at least 85%.

In yet another embodiment, disclosed is a process for coupling a chlorofluorocarbon comprising contacting 1,1,1-trichloro-2,2,2-trifluoroethane with hydrogen in the presence of a catalyst comprising ruthenium on a silicon carbide support, to produce a product mixture comprising 1,1,1,4,4,4-hexafluoro-2,3-dichloro-2-butene and hydrogen chloride, and recovering the 1,1,1,4,4,4-hexafluoro-2,3-dichloro-2-butene.

In yet another embodiment, disclosed is a process for the preparation of E- or Z-HFO-1336mzz comprising contacting hexafluoro-2-butyne with hydrogen at a ratio of 1:0.025 to 1:1.1 (molar ratio of hexafluoro-2-butyne in a reactor in the presence of a metallic catalyst at a temperature sufficient to cause hydrogenation of the triple bond of the hexafluoro-2-butyne producing a product stream comprising HFO-1336mzz and unreacted hexafluoro-2-butyne, wherein the catalyst is a metallic catalyst at a concentration of 100-5000 ppm dispersed over aluminum oxide, silicon carbide, or titanium silicates with a Ag or lanthanide poison, wherein the recycle ratio of reactant to product is between 1 and 9.

The foregoing general description and the following detailed description are exemplary and explanatory only and are not restrictive of the invention, as defined in the appended claims.

DETAILED DESCRIPTION

Disclosed is a process for the preparation of cis-1,1,1,4,4-hexafluoro-2-butene comprising contacting 1,1,1-trifluorotrichloroethane with hydrogen in the presence of a catalyst comprising ruthenium to produce a product mixture comprising 1316mxx, recovering said 1316mxx as a mixture of Z- and E-isomers, contacting said 1316mxx with hydrogen, in the presence of a catalyst selected from the group consisting of copper on carbon, nickel on carbon, copper and nickel on carbon and copper and palladium on carbon, to produce a second product mixture, comprising E- or Z-CFC-1326mxz, and subjecting said second product mixture to a separation step to provide E- or Z-1326mxz. The E- or Z-1326mxz can be dehydrochlorinated in an aqueous basic solution with an alkali metal hydroxide in the presence of a phase transfer catalyst to produce hexafluoro-2-butyne, which can then be selectively hydrogenated to produce Z-1,1,1,4,4,4-hexafluoro-2-butene using either Lindlar's catalyst, or a palladium catalyst further comprising a lanthanide element or silver.

In another embodiment, disclosed is a process for the preparation of fluorine-containing olefins comprising contacting a chlorofluoroalkene having the formula E- and Z-$CF_3CCl=CClCF_3$ with hydrogen in the presence of a catalyst comprising copper and palladium on a support, at a temperature of from about 150° C. to 250° C., to produce a product mixture comprising a fluorine-containing olefin having the formula E- or Z-$CF_3CH=CClCF_3$, or a mixture thereof, wherein the conversion of Z-$CF_3CCl=CClCF_3$ is at least 80% of the conversion of the Z-isomer, and the selectivity to the two isomers of $CF_3CH=CClCF_3$ is at least 85%.

In yet another embodiment, disclosed is a process for coupling a chlorofluorocarbon comprising contacting 1,1,1-trichloro-2,2,2-trifluoroethane with hydrogen in the presence of a catalyst comprising ruthenium on a silicon carbide support, to produce a product mixture comprising 1,1,1,4,4,4-hexafluoro-2,3-dichloro-2-butene and hydrogen chloride, and recovering the 1,1,1,4,4,4-hexafluoro-2,3-dichloro-2-butene.

In yet another embodiment, disclosed is a process for the preparation of E- or Z-HFO-1336mzz comprising contacting hexafluoro-2-butyne with hydrogen at a ratio of 1:0.025 to 1:1.1 (molar ratio of hexafluoro-2-butyne in a reactor in the presence of a metallic catalyst at a temperature sufficient to cause hydrogenation of the triple bond of the hexafluoro-2- butyne producing a product stream comprising HFO-1336mzz and unreacted hexafluoro-2-butyne, wherein the catalyst is a metallic catalyst at a concentration of 100-5000 ppm dispersed over aluminum oxide, silicon carbide, or titanium silicates with a Ag or lanthanide poison, wherein the recycle ratio of reactant to product is between 1 and 9.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

As used herein, chlorofluorocarbon is a C2, C3 or C4 alkane substituted completely with chlorine and fluorine, wherein all the chlorine substituents are on one terminal carbon of the molecule. Representative chlorofluorocarbons include 1,1,1-trichlorotrifluoroethane, 1,1,1-trichloro-pentafluoropropane, and 1,1,1-trichlorooctafluorobutane.

In one embodiment, disclosed is a process for the preparation of Z-HFO-1336mzz comprising dimerizing CFC-113a in the presence of a ruthenium catalyst to produce Z- and E-CFC-1316mxx, hydrogenating CFC-1316mxx in the presence of a catalyst to produce HCFO-1326mxz, dehydrochlorinating this to produce hexafluoro-2-butyne, and then hydrogenating the hexafluoro-2-butyne to produce Z-HFO1336mzz.

It has been previously reported, that two and three carbon chlorofluorocarbons can be dimerized to produce 4 carbon and 6 carbon chlorofluoroolefins, such as F1316mxx and F151-10mcxx, through reaction with hydrogen over a supported ruthenium catalyst. See U.S. Pat. No. 5,919,994. The chlorofluorocarbons included $CCl_3CF_3$ and $CCl_3CF_2CF_3$. The ruthenium catalyst could be supported on fluorided alumina, aluminum fluoride and fluorides of at least one metal selected from the group consisting of Zn, Mg, Ca, Ba, Y, Sm, Eu and Dy. Among the by-products produced were moderate amounts of two carbon compounds such as 1,1,1-trifluoroethane (HFC-143a), 1,1,1-trifluoro-2-chloroethane (HCFC-133a) or 1,1,1-trifluoro-2,2-dichloroethane (HCFC-123a), presumably formed from hydrogenolysis of one or more chlorine substituents. The dimerization produces 2 moles of HCl for each mole of CFC-113a reacted.

It has now been found that, while such catalysts are useful for hydrogenolysis reactions, they are less than optimal for dimerization reactions of this type. In particular, it has been observed that catalyst samples after use in coupling reactions for some period of time typically exhibit significant decreases in crush strength. In addition, for these reactions which produce hydrogen chloride as a reaction product from the coupling process, when the reactor effluent is scrubbed upon exiting the reactor, there is evidence of hydrogen fluoride in addition to hydrogen chloride, presumably from halogen exchange with the support. This would also necessitate the use of corrosion resistant materials of construction for the reactor materials.

It has now been found that ruthenium catalysts deposited on a silicon carbide support provide a catalyst which has higher crush strength, even after prolonged use. The ruthenium can be deposited on the support by techniques well known in the art, such as impregnation, or evaporation from solution. In one embodiment, the concentration of ruthenium on the support is typically in the range of from 0.1 weight percent to 5 weight percent. In another embodiment, the concentration of ruthenium on the support is from 0.25 weight percent to 3 weight percent. In yet another embodiment, the concentration of ruthenium on the support is from 0.5 weight percent to 2 weight percent. The crush strength of 2% ruthenium on calcium fluoride was observed to decrease from 6.6 pounds to 1.8 pounds after use in a reactor to convert 113a to 1316mxx for 12 hours. By comparison, the crush strength of a 1% ruthenium catalyst on silicon carbide was 45.1 pounds before use, and essentially unchanged after use for 12 hours.

The ruthenium can be deposited from any soluble ruthenium compound, including for example ruthenium halides, such as ruthenium chloride, or ruthenium nitrosyl nitrate.

The dimerization reaction in one embodiment is typically conducted at a temperature of from 150° C. to 300° C. In another embodiment, the dimerization reaction is conducted at from 150° C. to 240° C. In yet another embodiment the dimerization reaction is conducted at from 150° C. to 190° C. In one embodiment, the mole ratio of hydrogen to CFC-113a can be from 4:1 to 20:1. In another embodiment, the mole ratio of hydrogen to CFC-113a can be from 12:1 to 20:1. After scrubbing out hydrogen chloride, the product mixture comprising Z- and E-CFC-1316mxx can be recovered by distillation. Analysis of the scrubbing solution for halogen by ion chromatography indicates that for catalysts supported on $CaF_2$ that between 2.3% and 8.3% of the halogen in the scrubber solution is fluoride. Similar analysis of the scrubber solution for reactions run with catalysts supported on SiC find 0.6% of the halogen as fluoride.

Step II

Chlorofluoroalkenes can be converted to fluoroalkenes, fluoroalkynes or monochlorofluoroalkenes in the presence of hydrogen using catalysts containing of copper on carbon, copper on calcium fluoride, palladium on barium sulfate, palladium/barium chloride on alumina, Lindlar catalyst (palladium on $CaCO_3$, poisoned with lead), palladium on calcium fluoride poisoned with lead, copper and nickel on carbon, nickel on carbon, nickel on calcium fluoride, copper/nickel/chromium on calcium fluoride and unsupported alloys of copper and nickel. Other catalysts include catalysts comprising copper and nickel, nickel and chromium or copper, nickel and chromium. Still other catalysts include combinations of copper, nickel or chromium further comprising alkali metals such as potassium, cesium, rubidium or combinations thereof. Such catalysts may be supported on supports such as metal fluorides, alumina, and titanium dioxide, or unsupported.

Such catalysts can have relatively low rates of reactivity resulting in the need for large reactors to produce significant quantities on a commercial scale. In addition, chlorofluoroolefin 1316mxx is typically found as a mixture of the E- and Z-isomers, in a ratio of from about 3:2 to about 2:1. In practice, when using catalysts of copper supported on carbon or copper and nickel supported on carbon, the E-isomer is significantly more reactive than the Z-isomer. In order to obtain adequate conversion of the Z-isomer to HCFO-1326mxz, reactors need to be sized and conditions set to achieve adequate conversion of both the faster and slower reacting isomers.

Further, in order to obtain acceptable conversions, and reaction rates, with catalysts comprising copper, or copper and nickel, reaction temperatures of 300° C. and higher were typically required. However, copper metal begins to sublime at approximately 250° C., such that operating a reactor with a catalyst comprised of copper on a support, or copper and nickel on a support at temperature of 300° C. or higher would result in a coating of copper being deposited on the interior of the downstream components of the reactor system. Thus such a system and catalyst is not practical for use in a long term commercial production facility.

It has now been found that use of catalysts comprising copper combined with small amounts of palladium and supported on carbon can produce significant and unexpected improvements in both rate of reaction and selectivity. In one embodiment, the catalyst comprises from 0.1 to 1.0 weight percent palladium. In one embodiment, the catalyst comprises from 0.1 to 20 weight percent copper. In another embodiment, the catalyst comprises from 0.6 to 5.0 weight percent copper.

In one embodiment, the ratio of reactivity of the Z-isomer to the E-isomer is less than 2.5:1. In another embodiment, the ratio of reactivity of the Z-isomer to the E-isomer is less than 2.0:1. In yet another embodiment, the ratio of reactivity of the Z-isomer to the E-isomer is less than 1.5:1.

In one embodiment, the contact time for the process ranges from about 2 to about 120 seconds. In another embodiment, the contact time for the process ranges from 15 to 60 seconds.

In one embodiment, the ratio of hydrogen to chlorofluoroalkene is from about 1:1 to about 4:1. In another embodiment, the ratio of hydrogen to chlorofluoroalkene is from about 1:1 to about 2:1.

In one embodiment, the process for preparation of fluorine-containing olefins comprises reacting a chlorofluoroalkene with hydrogen in a reaction vessel constructed of an acid resistant alloy material. Such acid resistant alloy materials include stainless steels, high nickel alloys, such as Monel, Hastelloy, and Inconel. In one embodiment, the reaction takes place in the vapor phase.

In one embodiment, the temperature at which the process is run may be a temperature sufficient to cause replacement of the chlorine substituents with hydrogen. In another embodiment, the process is conducted at a temperature of from about 150° C. to about 300° C.

In some embodiments, the pressure for the hydrodechlorination reaction is not critical. In other embodiments, the process is performed at atmospheric or autogenous pressure. Means may be provided for the venting of the excess pressure of hydrogen chloride formed in the reaction and may offer an advantage in minimizing the formation of side products. In some embodiments, the process is conducted simply by flowing hydrogen and chlorofluoroalkene into the catalyst bed in a reactor at a specified temperature. In some embodiments the process is conducted by flowing hydrogen, chlorofluoroalkene and a carrier gas into the catalyst bed in the reactor. Examples of carrier gases include inert gases such as nitrogen, argon and helium.

Additional products of the reaction may include partially hydrodechlorinated intermediates; completely dechlorinated products, saturated hydrogenated compounds; various partially chlorinated intermediates or saturated compounds; and hydrogen chloride (HCl). For example, wherein the chlorofluoroalkene is 2,3-dichloro-1,1,1,4,4,4-hexafluoro-2-butene (CFC-1316mxx, E- and/or Z-isomers), the compounds formed in addition to E- and/or Z-1,1,1,4,4,4-hexafluoro-2-chloro-2-butene (E- and/or Z-HFC-1326mxz) may include, E- and/or Z-1,1,1,4,4,4-hexafluoro-2-butene (HFC-1336mzz), 1,1,1,4,4,4-hexafluorobutane (HFC-356mff), pentafluorobutane (HFC-1345, different isomers), 2-chloro-1,1,1,4,4,4-hexafluorobutane (HFC-346mdf), and 1,1,1,4,4,4-hexafluoro-2-butyne (HFB).

Step III

Also disclosed herein is a process for producing hexafluoro-2-butyne comprising, reacting Z-1,1,1,4,4,4-hexafluoro-2-chloro-2-butene HCFC-1326mxz) with an aqueous solution of an alkali metal hydroxide in the presence of a quaternary alkylammonium salt having alkyl groups of from four to twelve carbon atoms and mixtures thereof to produce a mixture comprising hexafluoro-2-butyne, and recovering the hexafluoro-2-butyne, wherein the conversion of Z-, 1,1,1,4,4,4-hexafluoro-2-chloro-2-butene to hexafluoro-2-butyne is at least 50% per hour.

Also disclosed is a process for producing hexafluoro-2-butyne comprising, reacting a fluorochloroolefin comprising E-1,1,1,4,4,4-hexafluoro-2-chloro-2-butene with an aqueous solution of an alkali metal hydroxide in the presence of a quaternary alkylammonium salt which comprises at least one alkyl group of at least 8 carbons, and recovering the hexafluoro-2-butyne, wherein the conversion of E-1,1,1,4,4,4-hexafluoro-2-chloro-2-butene to hexafluoro-2-butyne is at least 15% per hour.

Also disclosed is a process for producing hexafluoro-2-butyne comprising, reacting a fluorochloroolefin comprising Z- and E-1,1,1,4,4,4-hexafluoro-2-chloro-2-butene with an aqueous solution of an alkali metal hydroxide in the presence of a quaternary alkylammonium salt having alkyl groups of from four to twelve carbon atoms, and mixtures thereof, and a non-ionic surfactant, and recovering the hexafluoro-2-butyne, and wherein the conversion of Z- or E-1,1,1,4,4,4-hexafluoro-2-chloro-2-butene to hexafluoro-2-butyne is at least 20% per hour.

Hydrofluorochloroolefin HCFC-1326mxz is an impurity in some schemes for the synthesis of 1,1,1,4,4,4-hexafluoro-2-butene, which is of interest as a foam expansion agent. In other potential schemes, it can be an intermediate. One method of synthesis of HCFC-1326mxz is through the hydrogenation of 1,1,1,4,4,4-hexafluoro-2,3-dichloro-2-butene. Whatever the method of synthesis, one typically obtains a mixture of the Z- and E-stereoisomers about the double bond. Unfortunately, it exhibits rather high toxicity, so whether formed as an impurity, or as an intermediate, it is desirable to convert it into useful product in high yield. Dehydrochlorination would provide hexafluoro-2-butyne, which could be hydrogenated to provide 1,1,1,4,4,4-hexafluoro-2-butene. In classical organic chemistry, the dehydrochlorination of vinyl chlorides to form acetylenes requires rather harsh conditions, such as very strong bases, such as sodium in liquid ammonia. It has been reported that higher molecular weight polyfluorinated vinyl chlorides can be dehydrohalogenated to alkynes using aqueous base at temperatures of from 100-120° C. up to 200 or 250° C. At these temperatures however, hexafluoro-2-butyne would have too high a vapor pressure in a reactor, and be susceptible to degradation.

It has been found that Z- and E-1,1,1,4,4,4-hexafluoro-2-chloro-2-butene can be dehydrochlorinated at temperatures well below 100° C. using an aqueous basic solution in combination with quaternary alkylammonium salts as a phase transfer catalyst.

As used herein, phase transfer catalyst is intended to mean a substance that facilitates the transfer of ionic compounds into an organic phase from an aqueous phase or from a solid phase. The phase transfer catalyst facilitates the reaction of these dissimilar and incompatible components. While various phase transfer catalysts may function in different ways, their mechanism of action is not determinative of their utility in the present invention provided that the phase transfer catalyst facilitates the dehydrochlorination reaction.

A phase transfer catalyst as used herein is a quaternary alkylammonium salt wherein the alkyl groups are alkyl chains having from four to twelve carbon atoms. In one embodiment, the quaternary alkyl ammonium salt is a tetrabutylammonium salt. The anions of the salt can be halides such as chloride or bromide, hydrogen sulfate, or any other commonly used anion.

In another embodiment, the quaternary alkylammonium salt is trioctylmethylammonium chloride (Aliquat 336). In another embodiment, the quaternary alkylammonium salt is tetraoctylammonium chloride. In yet another embodiment, the quaternary alkylammonium salt is tetraoctylammonium hydrogen sulfate.

Other compounds commonly thought of as phase transfer catalysts in other applications, including crown ethers, cryptands or non-ionic surfactants alone, do not have a significant effect on conversion or the rate of the dehydrochlorination reaction in the same fashion.

The Z- and E-isomers of 1,1,1,4,4,4-hexafluoro-2-chloro-2-butene exhibit significantly different reactivities with respect to dehydrochlorination, and have different requirements for what functions as an effective phase transfer catalyst in this reaction. Dehydrochlorination of the Z-isomer $CF_3CCl=CHCF_3$ can be effected with quaternary alkylammonium salts wherein the alkyl groups are alkyl chains having from four to twelve carbon atoms. The anions of the salt can be halides such as chloride or bromide, hydrogen sulfate, or any other commonly used anion. In one embodiment, the quaternary alkyl ammonium salt is a tetrabutylammonium salt. In another embodiment, the quaternary alkylammonium salt is a tetrahexylammonium salt. In another embodiment, the quaternary alkylammonium salt is a tetraoctylammonumium salt. In yet another embodiment, the quaternary alkylammonium salt is a trioctylmethylammonumium salt.

Dehydrochlorination of the E-isomer of 1,1,1,4,4,4-hexafluoro-2-chloro-2-butene can be effected with quaternary alkylammonium salts, wherein the alkyl groups are alkyl chains having at least one alkyl chain of 8 carbons or more. In another embodiment, the quaternary alkylammonium salt has three alkyl chains of 8 carbons or more, such as trioctylmethylammonium salt. In yet another embodiment, the quaternary alkylammonium salt is a tetraoctylammonumium salt. In yet another embodiment, the quaternary ammonium salt is a tetradecylammonium salt. In yet another embodiment, the quaternary alkylammonium salt is a tetradodecylammonium salt. The anions of the salt can be halides such as chloride or bromide, hydrogen sulfate, or any other commonly used anion.

In yet another embodiment, dehydrochlorination of the E-isomer of 1,1,1,4,4,4-hexafluoro-2-chloro-2-butene can be effected with quaternary alkylammonium salts, wherein the alkyl groups are alkyl chains having from four to twelve carbon atoms, and in the presence of a non-ionic surfactant. The non-ionic surfactants can be ethoxylated nonylphenols, and ethoxylated C12 to C15 linear aliphatic alcohols. Suitable non-ionic surfactants include Bio-Soft® N25-9 and Makon® 10 are from Stepan Company.

In one embodiment, the quaternary alkylammonium salts is added in an amount of from 0.5 mole percent to 2.0 mole percent of the 1,1,1,4,4,4-hexafluoro-2-chloro-2-butene. In another embodiment, the quaternary alkylammonium salts is added in an amount of from 1 mole percent to 2 mole percent of the 1,1,1,4,4,4-hexafluoro-2-chloro-2-butene. In yet another embodiment, the quaternary alkylammonium salts is added in an amount of from 1 mole percent to 1.5 mole percent of the 1,1,1,4,4,4-hexafluoro-2-chloro-2-butene.

In one embodiment, the dehydrochlorination of Z- or E-1,1,1,4,4,4-hexafluoro-2-chloro-2-butene is conducted in the presence of an alkali metal halide salt. In one embodiment, the alkali metal is sodium or potassium. In one embodiment, the halide is chloride or bromide. In one embodiment, the alkali metal halide salt is sodium chloride. Without wishing to be bound by any particular theory, it is believed that the alkali metal halide salt stabilizes the phase transfer catalyst. Although the dehydrochlorination reaction itself produces alkali metal chloride, and in particular sodium chloride if sodium hydroxide is used as the base, addition of extra sodium chloride provides a further effect of increasing the yield of hexafluoro-2-butyne.

Addition of alkali metal halide salt also reduces the amount of fluoride ion measured in the water effluent from the reaction. Without wishing to be bound by any particular theory, the presence of fluoride is believed to result from decomposition of either the 1,1,1,4,4,4-hexafluoro-2-chloro-2-butene starting material, or the hexafluoro-2-butyne product.

In several samples, the amount of fluoride ion found in the water effluent from the dehydrochlorination is about 6000 ppm. In several examples, using from 30 to 60 equivalents of sodium chloride per mole of phase transfer catalyst, the amount of fluoride ion in the water effluent is reduced to 2000 ppm. In one embodiment, the alkali metal halide is added at from 25 to 100 equivalents per mole of phase transfer catalyst. In another embodiment, the alkali metal halide is added at from 30 to 75 equivalents per mole of phase transfer catalyst. In yet another embodiment, the alkali metal halide is added at from 40 to 60 equivalents per mole of phase transfer catalyst.

In one embodiment, the reaction is conducted at a temperature of from about 60 to 90° C. In another embodiment, the reaction is conducted at 70° C.

As used herein, the basic aqueous solution is a liquid (whether a solution, dispersion, emulsion, or suspension and the like) that is primarily an aqueous liquid having a pH of over 7. In some embodiments the basic aqueous solution has a pH of over 8. In some embodiments, the basic aqueous solution has a pH of over 10. In some embodiments, the basic aqueous solution has a pH of 10-13. In some embodiments, the basic aqueous solution contains small amounts of organic liquids which may be miscible or immiscible with water. In some embodiments, the liquid medium in the basic aqueous solution is at least 90% water. In one embodiment the water is tap water; in other embodiments the water is deionized or distilled.

The base in the aqueous basic solution is selected from the group consisting of hydroxide, oxide, carbonate, or phosphate salts of alkali, alkaline earth metals and mixtures thereof. In one embodiment, bases which may be used lithium hydroxide, sodium hydroxide, potassium hydroxide, calcium hydroxide, magnesium oxide, calcium oxide, sodium carbonate, potassium carbonate, sodium phosphate, potassium phosphate, or mixtures thereof.

Step IV

In one embodiment, the process is a method for the synthesis of Z-HFO-1336mzz from hexafluoro-2-butyne in high selectivity by selective hydrogenation in the presence of particular catalysts.

In one embodiment, the catalyst is a Palladium catalyst dispersed on aluminum oxide or titanium silicate, doped with silver and/or a lanthanide, with a low loading of palladium. In one embodiment, the palladium loading is from 100 ppm to 5000 ppm. In another embodiment, the palladium loading is from 200 ppm to 5000 ppm. In one embodiment, the catalyst is doped with at least one of silver, cerium or lanthanum. In one embodiment, the mole ratio of cerium or lanthanum to palladium is from 2:1 to 3:1. In one embodiment the mole ratio of silver to palladium is about 0.5:1.0.

In another embodiment, a Lindlar catalyst is used, which is a heterogeneous palladium catalyst on a calcium carbonate support, which has been deactivated or conditioned with a lead compound. The lead compound can be lead acetate, lead oxide, or any other suitable lead compound. In one embodiment, the catalyst is prepared by reduction of a palladium salt in the presence of a slurry of calcium carbonate, followed by the addition of the lead compound. In one embodiment, the palladium salt is palladium chloride. In another embodiment, the catalyst is deactivated or conditioned with quinoline. In one embodiment, the amount of the catalyst used is from about 0.5% by weight to about 4% by weight of the amount of the fluorinated alkyne. In another embodiment, the amount of the catalyst used is from about 1% by weight to about 3% by weight of the amount of the fluorinated alkyne. In yet another embodiment, the amount of the catalyst used is from about 1% to about 2% by weight of the amount of the fluorinated alkyne.

In one embodiment, the process is conducted in a batchwise process. In another embodiment, the process is conducted in a continuous process in the gas phase.

In one embodiment, reaction of the fluorinated alkynes with hydrogenation in the presence of the catalyst should be done with addition of hydrogen in portions, with increases in the pressure of the vessel of no more than about 100 psi with each addition. In another embodiment, the addition of hydrogen is controlled so that the pressure in the vessel increases no more than about 50 psi with each addition. In one embodiment, after enough hydrogen has been consumed in the hydrogenation reaction to convert at least 50% of the fluorinated alkyne to alkene, hydrogen can be added in larger increments for the remainder of the reaction. In another embodiment, after enough hydrogen has been consumed in the hydrogenation reaction to convert at least 60% of the fluorinated alkyne to alkene, hydrogen can be added in larger increments for the remainder of the reaction. In yet another embodiment, after enough hydrogen has been consumed in the hydrogenation reaction to convert at least 70% of the fluorinated alkyne to alkene, hydrogen can be added in larger increments for the remainder of the reaction. In one embodiment, the larger increments of hydrogen addition can be 300 psi. In another embodiment, the larger increments of hydrogen addition can be 400 psi.

In one embodiment, the amount of hydrogen added is about one molar equivalent per mole of fluorinated alkyne. In another embodiment, the amount of hydrogen added is from about 0.9 moles to about 1.3 moles, per mole of fluorinated alkyne. In yet another embodiment, the amount of hydrogen added is from about 0.95 moles to about 1.1 moles, per mole of fluorinated alkyne. In yet another embodiment, the amount of hydrogen added is from about 0.95 moles to about 1.03 moles, per mole of fluorinated alkyne.

In one embodiment, the hydrogenation is performed at ambient temperature. In another embodiment, the hydrogenation is performed at above ambient temperature. In yet another embodiment, the hydrogenation is performed at below ambient temperature. In yet another embodiment, the hydrogenation is performed at a temperature of below about 0° C.

In an embodiment of a continuous process, a mixture of fluorinated alkyne and hydrogen are passed through a reaction zone containing the catalyst. In one embodiment, the molar ratio of hydrogen to fluorinated alkyne is about 1:1. In another embodiment of a continuous process, the molar ratio of hydrogen to fluorinated alkyne is less than 1:1. In yet another embodiment, the molar ratio of hydrogen to fluorinated alkyne is about 0.67:1.0.

In one embodiment of a continuous process, the reaction zone is maintained at ambient temperature. In another embodiment of a continuous process, the reaction zone is maintained at a temperature of 30° C. In yet another embodiment of a continuous process, the reaction zone is maintained at a temperature of about 40° C. In yet another embodiment of a continuous process, the reaction zone is maintained at a temperature of from 60° C. to 90° C.

In one embodiment of a continuous process, the flow rate of fluorinated alkyne and hydrogen is maintained so as to provide a residence time in the reaction zone of about 30 seconds. In another embodiment of a continuous process, the flow rate of fluorinated alkyne and hydrogen is maintained so as to provide a residence time in the reaction zone of about 15 seconds. In yet another embodiment of a continuous process, the flow rate of fluorinated alkyne and hydrogen is maintained so as to provide a residence time in the reaction zone of about 7 seconds.

It will be understood, that contact time in the reaction zone is reduced by increasing the flow rate of fluorinated alkyne and hydrogen into the reaction zone. As the flow rate is increased this will increase the amount of fluorinated alkyne being hydrogenated per unit time. Since the hydrogenation is exothermic, depending on the length and diameter of the reaction zone, and its ability to dissipate heat, at higher flow rates it may be desirable to provide a source of external cooling to the reaction zone to maintain a desired temperature.

In one embodiment of a continuous process, the mixture of fluorinated alkyne and hydrogen further comprises an inert carrier gas. In one embodiment, the inert carrier gas is selected from the group consisting of nitrogen, helium or argon. In one embodiment, the inert carrier gas is from about 10% to about 80% of the gas fed to the continuous process. In another embodiment, the inert carrier gas is from about 20% to about 50% of the gas fed to the continuous process.

In one embodiment of a continuous process, the amount of palladium on the support in the Lindlar catalyst is 5% by weight. In another embodiment, the amount of palladium on the support in the Lindlar catalyst is greater than 5% by weight. In yet another embodiment, the amount of palladium on the support can be from about 5% by weight to about 1% by weight.

In one embodiment, upon completion of a batch-wise or continuous hydrogenation process, the cis-dihydrofluoroalkene can be recovered through any conventional process, including for example, fractional distillation. In another embodiment, upon completion of a batch-wise or continuous hydrogenation process, the cis-dihydrorofluoroalkene is of sufficient purity to not require further purification steps.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

EXAMPLES

The concepts described herein will be further described in the following examples, which do not limit the scope of the invention described in the claims.

Example 1

Example 1 demonstrates the preparation of a ruthenium catalyst supported on silicon carbide from ruthenium chloride.

In this experiment, fifty grams (50 gm) of SiC support is added to 2.632 gm of $RuCl_3(H_2O)_3$ in just enough water to wet the SiC. The sample is mixed using a vortexer at a 1400 speed setting. Vortex the mixture for 15-20 seconds then allow to set for 5 minutes. This will be repeated several times over a period of 30-60 minutes, until all excess water is absorbed. Allow the sample to air dry inside the beaker for an hour before removing the sample and placing on a screen to air dry. Once the sample is visibly air dried, place it inside a quartz boat and in the furnace. Heat to 125° C. for 4 hours, then 250° C. for 4 hours under nitrogen.

Example 2

Example 2 demonstrates the preparation of a ruthenium catalyst supported on silicon carbide from ruthenium nitrosyl nitrate.

In this experiment, fifty grams (50 gm) of SiC support is added to 3.208 gm of $Ru(NO)NO_3$ and 1.42 gm of triethanolamine in just enough water to wet the SiC. The sample is mixed using a vortexer at a 1400 speed setting. Vortex the mixture for 15-20 seconds then allow to set for 5 minutes. This will be repeated several times over a period of 30-60 minutes, until all excess water is absorbed. Allow the sample to air dry inside the beaker for an hour before removing the sample and placing on a screen to air dry. Once the sample is visibly air dried, place it inside a quartz boat and in the furnace. Heat to 125° C. for 4 hours, then 250° C. for 4 hours under nitrogen.

Example 3

Example 3 demonstrates the conversion of 113a to 1316mxx over 1% Ru/SiC catalyst.

An inconel tube (½ inch OD) was filled with 2 cc (1.07 gm) of 1% Ru/SiC ⅛" pellets. The temperature of the catalyst bed was raised to 120° C. and purged with hydrogen (50 sccm) for 60 minutes and then at 250° C. for 180 minutes. The temperature was then lowered to 175° C. for 120 minutes while maintaining a hydrogen flow of 20 sccm. The temperature was lowered to 160° C. and the flow of CFC-113a ($CF_3CCl_3$) set to 2.31 ml/hour and the hydrogen to 32 sccm. The reactor effluent was analyzed every hour via online GCMS and then the results averaged to give the values in the table below. The temperature was raised to 170° C. and the effluent analyzed every hour for four hours, averaged, and shown in the table below.

TABLE 1

| % 143a | % 114a | % 123 | % 113a | % Z-1316 | % E-1316 | % 316maa | Temp (C.) |
|---|---|---|---|---|---|---|---|
| 4.1 | 2.1 | 2.8 | 60 | 18.4 | 11.7 | 0.3 | 160 |
| 4.9 | 2.2 | 2.8 | 57.4 | 19.6 | 12.0 | 0.4 | 170 |

Example 4

Example 4 demonstrates the conversion of 113a to 1316mxx over 2% Ru catalyst.

An inconel tube (½ inch OD) was filled with 2 cc (1.07 gm) of 2% Ru supported on ⅛" pellets either on SiC or $CaF_2$. The temperature of the catalyst bed was raised to 120° C. and purged with hydrogen (50 sccm) for 60 minutes and then at 250° C. for 180 minutes. The temperature was then lowered to 175° C. for 120 minutes while maintaining a hydrogen flow of 20 sccm. The temperature was lowered to 160° C. and the flow of CFC-113a ($CF_3CCl_3$) set to 2.31 ml/hour and the hydrogen to 32 sccm. The reactor effluent was analyzed every hour via online GCMS and then the results averaged to give the values in the table below. The temperature was raised to 170° C. and the effluent analyzed every hour for four hours, averaged, and shown in the table below.

TABLE 2

| Support | % 143a | % 114a | % 123 | % 113a | % Z-1316 | % E-1316 | % 316maa | Temp (C.) |
|---|---|---|---|---|---|---|---|---|
| SiC | 1.9 | 2.0 | 1.3 | 53.0 | 24.0 | 16.7 | 0.6 | 160 |
| SiC | 2.7 | 2.1 | 1.7 | 45.5 | 28.8 | 17.9 | 0.7 | 170 |
| CaF$_2$ | 0.8 | 2.2 | 2.7 | 59.5 | 22.8 | 10.9 | 1.0 | 160 |
| CaF$_2$ | 0.8 | 2.1 | 2.2 | 55.5 | 25.2 | 12.1 | 1.3 | 170 |

Example 5

Example 5 demonstrates the conversion of CFC-1316mxx to HFC-1326mzz over Pd/Cu on carbon catalyst.

An Inconel® tube (⅝ inch OD) was filled with 13 cc (5.3 gm) of Pd/Cu on acid washed carbon (18-30 mesh). The temperature of the reactor was raised to 100° C. for 30 minutes under N2 flow (30 sccm, $5.0 \times 10^{-7}$ m$^3$/sec). The temperature was then increased to 200° C. under H$_2$ flow for one hour. The catalysts and flows were changed as described in the experiments in Table 3, below, and the reactor effluent was analyzed by GCMS to provide the following molar percent of products.

TABLE 3

| Catalyst | CT (sec) | Molar ratio H$_2$/1316 | Reactor effluent concentration (molar %) | | | | | | |
|---|---|---|---|---|---|---|---|---|---|
| | | | t-1336 | 356mff | 1345 | c-1336 | 346mdf | 1316mxx | 1326 |
| Pd/Cu/C | 30 | 2:1 | 0.17 | 0 | 0 | 0.09 | 0.13 | 46.31 | 52.98 |
| Pd/CaF2 | 30 | 2:1 | 4.8 | 9.3 | 0 | 13.2 | 2.3 | 53.5 | 11.4 |

Example 6

Example 6 demonstrates the conversion of CFC-1316mxx to HFC-1336mzz with Pd/Cu on carbon catalyst.

A Hastelloy reactor 10"L×½" o.d.×0.034" wall was filled with 11 cc of the catalyst. The catalyst was conditioned at 150° C. for 65 hrs in hydrogen flow of 50 sccm ($8.3 \times 10^{-7}$ m$^3$/sec). The hydrodechlorination of 1316mxx was studied at temperatures of 240° C. using Pd/Cu on carbon or Pd/BaCl2 on alumina, as indicated in Table 4. Products of the reaction were analyzed by GCMS to give the following molar concentrations.

TABLE 4

| Cat. | CT (sec) | Molar ratio H$_2$/1316mxx | Reactor effluent concentration (molar %) | | | | | | | |
|---|---|---|---|---|---|---|---|---|---|---|
| | | | t-1336 | 1345 | 356mff | c-1336 | t-1326 mxz | c-1326 mxz | t-1316 mxx | c-1316 mxx |
| Pd/Cu/C | 30 | 1:1 | 5.1 | 0 | 0.43 | 0.58 | 69.35 | 5.75 | 7.64 | 5.31 |
| Pd/BaCl2 | 30 | 1:1 | 11.39 | 0.57 | 7.81 | 1.13 | 20.35 | 0.64 | 49.21 | 1.79 |

Example 7

Example 7 demonstrates the effect of catalyst on degree of conversion of E- and Z-1326mxz.

A Hastelloy reactor 5"L×½" o.d.×0.034" wall was filled with 3 cc of either 0.6% Pd/5.5% Cu/C, or Ni/Cu/C catalyst. The catalyst was conditioned at 150° C. for 65 hrs in hydrogen flow of 50 sccm ($8.3 \times 10^{-7}$ m$^3$/sec).

Example 8

Example 8 demonstrates the conversion of CFC-1316mxx to HFC-1336mzz over Cu on carbon catalyst.

In a 400 ml Pyrex beaker a solution of 10.73 g CuCl$_2$.2H$_2$O was prepared in 65 ml of 10% HCl in deionized water. 46.0 g of acid washed carbon (10/30 mesh) was added to the solution. The stiff slurry was allowed to stand at room temperature for 1 hr with occasional stirring. Then the slurry was dried at 110-120° C. under air overnight. After that the catalyst was transferred into quartz tube which was purged with 500 sccm ($8.3 \times 10^{-6}$ m$^3$/sec) N2 at 25° C. for 15 min, then 100 sccm each He and H$_2$ for 15 min. Then the catalyst was heated at 5° C./min to 500° C. for 6 hrs in He/H$_2$. The procedure gave 48.52 g of catalyst.

A Hastelloy reactor 10"L×½" o.d.×0.034" wall was filled with 11 cc (4.73 g) of 8% Cu on acid washed carbon catalyst. The catalyst was conditioned at 150° C. for 16 hrs in hydrogen flow of 50 sccm ($8.3 \times 10^{-7}$ m$^3$/sec). The temperature was raised to 350° C. for 2 hrs in hydrogen flow of 50 sccm ($8.3 \times 10^{-7}$ m$^3$/sec). The hydrodechlorination of 1316mxx was studied at temperatures ranging from about 300 to 400° C. as indicated in Table 5, below. Products of the reaction were analyzed by GCMS to give the following molar concentrations.

TABLE 5

| Temp °C. | CT (sec) | Molar ratio H$_2$/1316 | Reactor effluent concentration (molar %) | | | | | | | |
|---|---|---|---|---|---|---|---|---|---|---|
| | | | t-1336 | 1345 | 356mff | c-1336 | t-1326 mxz | c-1326 mxz | t-1316 mxx | c-1316 mxx |
| 300 | 30 | 4:1 | 0.58 | 0.0 | 0.40 | 0.09 | 31.47 | 1.65 | 34.41 | 29.85 |
| 300 | 60 | 4:1 | 1.65 | 0.0 | 1.18 | 0.12 | 73.93 | 4.16 | 5.16 | 11.72 |
| 340 | 60 | 4:1 | 27.34 | 0.06 | 0.90 | 1.38 | 66.35 | 2.87 | 0.0 | 0.0 |
| 340 | 75 | 5:1 | 56.81 | 1.18 | 3.42 | 3.25 | 32.00 | 1.14 | 0.0 | 0.0 |
| 325 | 75 | 5:1 | 35.80 | 0.66 | 2.62 | 2.63 | 53.64 | 2.05 | 0.0 | 0.0 |
| 360 | 75 | 5:1 | 68.83 | 2.54 | 5.14 | 3.21 | 17.76 | 0.63 | 0.0 | 0.0 |
| 360 | 75 | 5:1 | 66.08 | 2.63 | 5.27 | 3.39 | 19.91 | 0.68 | 0.0 | 0.0 |
| 400 | 75 | 5:1 | 65.00 | 9.13 | 17.40 | 2.10 | 0.48 | 0.00 | 0.0 | 0.0 |
| 400 | 50 | 5:1 | 69.78 | 5.93 | 8.94 | 4.39 | 7.07 | 0.08 | 0.0 | 0.0 |

Example 9

Example 9 demonstrates the conversion of CFC-1316mxx to HFC-1336 over Cu/Ni on carbon catalyst.

A Hastelloy reactor 15"L×1" o.d.×0.074" wall was filled with 23 cc (8.7 g) of 1% Cu/1% Ni on carbon catalyst. The catalyst was conditioned with 50 sccm ($8.3 \times 10^{-7}$ m$^3$/sec) of hydrogen flow according to the following protocol: 1 hr at 50° C., followed by 1 hr at 100° C., followed by 1 hr at 150° C., followed by 1 hr at 200° C., followed by 1 hr at 250° C., followed by 2 hr at 300° C., followed by a final 16 hrs at 200° C.

The hydrodechlorination of 1316mxx was studied over a temperature range of 200-375° C. Products of the reaction were analyzed by GCMS to give the molar concentrations as listed in Table 6.

TABLE 6

| Temp | CT | Molar ratio | Reactor effluent concentration (molar %) | | | | | |
|---|---|---|---|---|---|---|---|---|
| ° C. | (sec) | H$_2$/1316 | t-1336 | c-1336 | t-1326mxz | c-1326mxz | t-1316mxx | c-1316mxx |
| 200 | 75 | 5:1 | 0.14 | 0.47 | 40.50 | 1.24 | 51.34 | 5.38 |
| 300 | 75 | 5:1 | 7.10 | 0.61 | 87.28 | 3.91 | 0.08 | 0.12 |
| 300 | 75 | 7.5:1 | 34.31 | 4.04 | 58.68 | 1.64 | 0.00 | 0.00 |
| 350 | 30 | 7.5:1 | 60.33 | 6.51 | 29.96 | 0.47 | 0.00 | 0.00 |
| 375 | 30 | 7.5:1 | 75.71 | 6.98 | 8.41 | 0.05 | 0.00 | 0.00 |

Example 10

Example 10 demonstrates the selective hydrogenation of hexafluoro-2-butyne with Lindlar's catalyst.

5 g of Lindlar (5% Pd on CaCO3 poisoned with lead) catalyst was charged in 1.3 L rocker bomb. 480 g (2.96 mole) of hexafluoro-2-butyne was charged in the rocker. The reactor was cooled down (−78° C.) and evacuated. After the bomb was warmed up to room temperature, H$_2$ was added slowly, by increments which did not exceed Δp=50 psi. A total of 3 moles H$_2$ were added to the reactor. A gas chromatographic analysis of the crude product indicated the mixture consisted of CF$_3$C≡CCF$_3$ (0.236%), trans-isomer of CF$_3$CH═CHCF$_3$ (0.444%), saturated CF$_3$CH$_2$CH$_2$CF$_3$ (1.9%) CF$_2$═CHCl, impurity from starting butyne, (0.628%), cis-isomer of CF$_3$CH═CHCF$_3$ (96.748%). Distillation afforded 287 g (59% yield) of 100% pure cis-CF$_3$CH═CHCF$_3$ (boiling point 33.3° C.).

Example 11

Example 11 demonstrates the hydrogenation of hexafluoro-2-butyne over a catalyst of 200 ppm Pd on alumina, and doped 3:1 with cerium.

A Hastelloy tube reactor 8" long with a 1" O.D. (outside diameter) and 0.074" wall thickness was filled with 3 g of catalyst. The catalyst was conditioned at 70° C. with a flow of nitrogen (50 sccm) and hydrogen (10 sccm) for one hour at 200 C. The reactor was cooled to 82 C. A mixture of hexafluoro-2-butyne (5.5 sccm), hydrogen (1.6 sccm) and nitrogen (454 sccm) were then flowed into the reactor with a back pressure of 50 psig. The product mixture was collected in a cold trap after exiting the reactor and analyzed by gas chromatography. The product mixture was found to contain CF$_3$CH═CHCF$_3$ (cis) (36.5%), CF$_3$CH═CHCF$_3$ (trans) (1.6%), CF$_3$CH$_2$CH$_2$CF$_3$ (0.43%) and unreacted CF$_3$C≡CCF$_3$ (60.8%).

Example 12

Example 12 demonstrates the hydrogenation of hexafluoro-2-butyne over a catalyst of 200 ppm Pd on alumina, and doped 2:1 with lanthanum.

A Hastelloy tube reactor 8" long with a 1" O.D. (outside diameter) and 0.074" wall thickness was filled with 3 g of catalyst. The catalyst was conditioned at 70° C. with a flow of nitrogen (50 sccm) and hydrogen (10 sccm) for one hour at 200 C. The reactor was cooled to 74 C. A mixture of hexafluoro-2-butyne (5.8 sccm), hydrogen (2.0 sccm) and nitrogen (455 sccm) were then flowed into the reactor with a back pressure of 50 psig. The product mixture was collected in a cold trap after exiting the reactor and analyzed by gas chromatography. The product mixture was found to contain CF$_3$CH═CHCF$_3$ (cis) (34.3%), CF$_3$CH═CHCF$_3$ (trans) (0.95%), CF$_3$CH$_2$CH$_2$CF$_3$ (0.08%) and unreacted CF$_3$C≡CCF$_3$ (64.7%).

Example 13

Example 13 demonstrates the hydrogenation of hexafluoro-2-butyne in a continuous process to produce a mixture of cis- and trans-1,1,1,4,4,4-hexafluoro-2-butene.

A Hastelloy tube reactor 10" long with a 5" O.D. (outside diameter) and 0.35" wall thickness was filled with 10 g of Lindlar catalyst. The catalyst was conditioned at 70° C. with a flow of hydrogen for 24 hours. Then a flow of a 1:1 mole ratio of hexafluoro-2-butyne and hydrogen was passed through the reactor at 30° C. at a flow rate sufficient to provide a 30 second contact time. The product mixture was collected in a cold trap after exiting the reactor and analyzed by gas chromatography. The product mixture was found to contain CF$_3$CH═CHCF$_3$ (cis) (72%), CF$_3$CH═CHCF$_3$ (trans) (8.8%), CF$_3$CH$_2$CH$_2$CF$_3$ (7.8%) and CF$_3$C≡CCF$_3$ (3.3%).

Example 14

Example 14 demonstrates the hydrogenation of hexafluoro-2-butyne in a continuous process with a hydrogen:alkyne mole ratio of 0.67:1.

The procedure of example 13 was followed, with the exception that the mole ratio of hydrogen:hexafluoro-2-butyne fed to the reactor was 0.67:1.0. Analysis of the product mixture indicated CF$_3$CH═CHCF$_3$ (cis) (65.3%), CF$_3$CH═CHCF$_3$ (trans) (4.4%), CF$_3$CH$_2$CH$_2$CF$_3$ (3.4%) and CF$_3$C≡CCF$_3$ (23.5%).

Example 15

Example 15 demonstrates the hydrogenation of hexafluoro-2-butyne in a continuous process with a 7 second contact time.

The procedure of example 13 was followed, with the exception that the flow rate was adjusted to provide a contact time of 7 seconds. The reaction was slightly exothermic, with the reactor warming to 42° C. Analysis of the product mixture indicated CF$_3$CH=CHCF$_3$ (cis) (72.5%), CF$_3$CH=CHCF$_3$ (trans) (8.7%), CF$_3$CH$_2$CH$_2$CF$_3$ (8.6%) and CF$_3$C≡CCF$_3$ (6.9%).

Example 16

NaOH aqueous solution (12 mL, 0.12 mol) was added to the mixture of Z-1326 (20 g, 0.1 mol) and water (18 mL) in the presence of Tetra-n-butylammonium bromide (0.45 g, 0.001325 mol) at 35° C. The reaction temperature was raised to 70° C. after the addition, and gas chromatography was used to monitor the reaction. The reaction was completed after 1 hour and 15.4 g product (conversion: 100%; yield: 95%) was collected in a dry ice trap.

Example 17

NaOH aqueous solution (12 mL, 0.12 mol) was added to the mixture of Z-1326 (20 g, 0.1 mol) and water (18 mL) in the presence of Aliquat® 336 (0.53 g, 0.001325 mol) at 35° C. The reaction temperature was raised to 70° C. after the addition, and gas chromatography was used to monitor the reaction. The reaction was completed after 1 hour and 15.6 product (conversion: 100%; yield: 96%) was collected in a dry ice trap.

Example 18

NaOH aqueous solution (12 mL, 0.12 mol) was added to the mixture of E-1326 (20 g, 0.1 mol) and water (18 mL) in the presence of Aliquat® 336 (0.53 g, 0.001325 mol) at 42° C. The reaction temperature was raised to 70° C. after the addition, and gas chromatography was used to monitor the reaction. The reaction was completed after 1 hours and 15.8 g product (conversion: 100%; yield: 98%) was collected in a dry ice trap.

Example 19

NaOH aqueous solution (12 mL, 0.12 mol) was added to the mixture of E-1326 (20 g, 0.1 mol) and water (18 mL) in the presence of Tetraoctylammonium bromide (0.72 g, 0.001325 mol) at 42° C. The reaction temperature was raised to 70° C. after the addition, and gas chromatography was used to monitor the reaction. The reaction was completed after six and half hours. 15.6 g product (conversion: 100%; yield: 95%) was collected in a dry ice trap.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process for the preparation of cis-1,1,1,4,4,4-hexafluoro-2-butene comprising:
   a) contacting 1,1,1-trifluorotrichloroethane with hydrogen in the presence of a catalyst comprising ruthenium to produce a product mixture comprising 1316mxx;
   b) recovering said 1316mxx as a mixture of Z- and E-isomers;
   c) contacting said 1316mxx with hydrogen, in the presence of a catalyst selected from the group consisting of copper on carbon, nickel on carbon, copper and nickel on carbon and copper and palladium on carbon, to produce a second product mixture, comprising E- or Z-CFC-1326mxz;
   d) subjecting said second product mixture to a separation step to provide E- or Z-1326mxz; and
   e) further comprising contacting said E- or Z-CFC1326mxz with an aqueous solution of an alkali metal hydroxide in the presence of a phase transfer catalyst to produce hexafluoro-2-butyne; and;
   f) further comprising contacting said hexafluoro-2-butyne with hydrogen in the presence of a catalyst of palladium on a support, and at least one element selected from the group consisting of lanthanum, cerium and silver, to produce cis-1,1,1,4,4,4-hexafluoro-2-butene.

2. The process of claim 1, wherein step e) comprises further contacting said E- or Z-1326mxz with an aqueous solution of an alkali metal hydroxide in the presence of a quaternary alkylammonium salt having alkyl groups of from four to twelve carbon atoms and mixtures thereof, wherein at least said Z-1326mxz is converted to produce a mixture comprising hexafluoro-2-butyne, and recovering the hexafluoro-2-butyne.

3. The process of claim 1, wherein step e) comprises further contacting said E- or Z-1326mxz with an aqueous solution of an alkali metal hydroxide in the presence of a quaternary alkylammonium salt which comprises at least one alkyl group of at least 8 carbons, wherein at least said E-1326mxz is converted to produce a mixture comprising hexafluoro-2-butyne, and recovering the hexafluoro-2-butyne.

4. The process of claim 2 or 3, wherein the alkali metal hydroxide further comprises an alkali metal halide.

5. The process of claim 1, wherein the catalyst for the first contacting step is ruthenium supported on calcium fluoride or ruthenium supported on silicon carbide.

6. A process for the preparation of fluorine-containing olefins comprising contacting a chlorofluoroalkene having the formula E- and Z-CF$_3$CCl=CClCF$_3$ with hydrogen in the presence of a catalyst comprising copper and palladium on a support, at a temperature of from about 150° C. to 250° C., to produce a product mixture comprising a fluorine-containing olefin having the formula E- or Z-CF$_3$CH=CClCF$_3$, or a mixture thereof, wherein the conversion of Z-CF$_3$CCl=CClCF$_3$ is at least 80% of the conversion of the E-isomer, and the selectivity to the two isomers of CF$_3$CH=CClCF$_3$ is at least 85%.

7. The process of claim 6, wherein said support is carbon.

8. The process of claim 6, wherein the process is conducted at a temperature of from 175° C. to 250° C.

9. The process of claim 6, wherein the ratio of hydrogen to E- or Z-CF$_3$CCl=CClCF$_3$ 1:1 to 8:1.

10. The process of claim 6, wherein the ratio of hydrogen to E- or Z-$CF_3CCl\!=\!CClCF_3$ 1:1 to 2:1.

11. The process of claim 6, wherein the selectivity for the production of E- or Z-$CF_3CH\!=\!CClCF_3$ is at least 90%.

12. The process of claim 6, wherein the selectivity for the production of E- or Z-$CF_3CH\!=\!CClCF_3$ is at least 95%.

* * * * *